US00PP37562P2

(12) United States Plant Patent
van Dijk

(10) Patent No.: US PP37,562 P2
(45) Date of Patent: Aug. 4, 2026

(54) ***ANTHURIUM* PLANT NAMED 'AN2636445'**

(50) Latin Name: *Anthurium andreanum*
Varietal Denomination: AN2636445

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/315,588

(22) Filed: Aug. 31, 2025

(51) Int. Cl.
*A01H 5/02* (2018.01)
*A01H 6/00* (2018.01)

(52) U.S. Cl.
USPC ..... Plt./365
CPC ..... *A01H 6/00* (2018.05)

(58) Field of Classification Search
USPC ..... Plt./365
CPC ... A01H 5/02; A01H 5/00; A01H 6/10; A01H 6/00
See application file for complete search history.

(56) References Cited

U.S. PATENT DOCUMENTS

PP34,200 P2 * 5/2022 Van Dijk ..... Plt./365

* cited by examiner

*Primary Examiner* — June Hwu
(74) *Attorney, Agent, or Firm* — C. Anne Whealy

(57) ABSTRACT

A new and distinct cultivar of *Anthurium* plant named 'AN2636445', characterized by its upright to outwardly arching plant habit; freely clumping growth habit; bushy and dense plants; ovate-cordate dark green-colored leaves; freely flowering habit; open inflorescences that are positioned above the foliar plane on strong scapes; ovate-cordate spathes that are reddish orange in color with white-colored venation; and yellow to yellowish white to white-colored spadices.

2 Drawing Sheets

Figure 1:
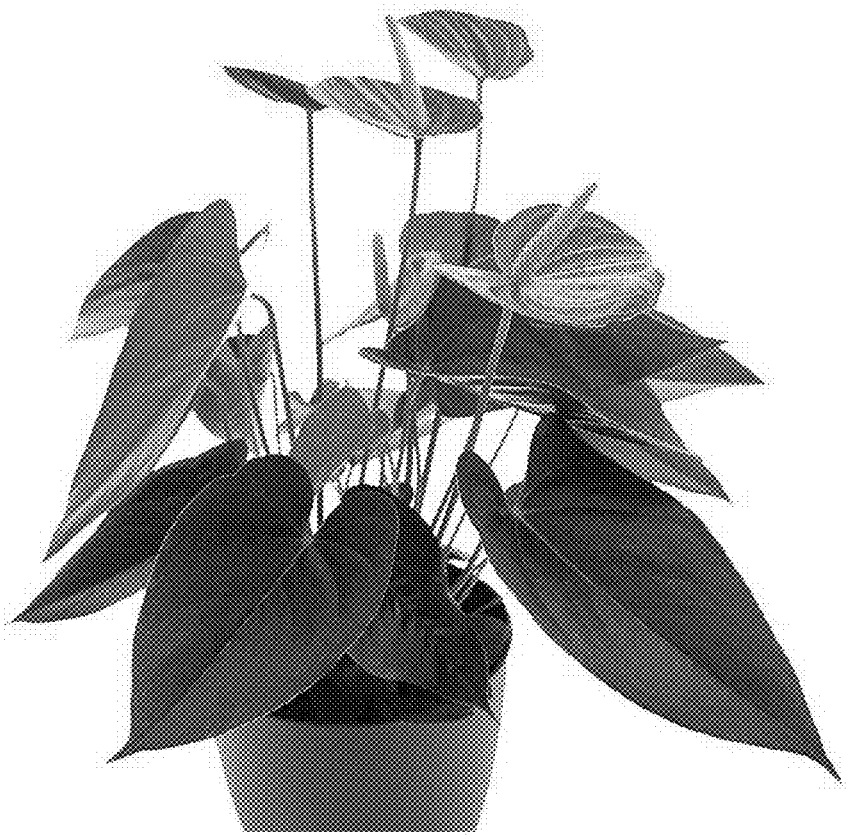

Botanical designation: *Anthurium andreanum.*
Cultivar denomination: 'AN2636445'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2695. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2636445'.

The new *Anthurium* plant is a product of a controlled breeding program conducted by the Inventor in Bleiswijk, The Netherlands. The objective of the breeding program is to create new *Anthurium* plants with durable reddish orange-colored spathes with white-colored venation.

The new *Anthurium* plant originated from a cross-pollination made by the Inventor in September 2013 in Bleiswijk, The Netherlands of a proprietary breeding selection of *Anthurium andreanum* identified as code number 11-026533-0004, not patented, as the female, or seed, parent with a proprietary breeding selection of *Anthurium andreanum* identified as code number 11-026521-0004, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December, 2015.

Asexual reproduction of the new *Anthurium* plant by in vitro meristem propagation in a controlled environment in Bleiswijk, The Netherlands since November, 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2636445'. These characteristics in combination distinguish 'AN2636445' as a new and distinct *Anthurium* plant:

1. Upright to outwardly arching plant habit.
2. Freely clumping growth habit; bushy and dense plants.
3. Ovate-cordate dark green-colored leaves.
4. Freely flowering habit.
5. Open inflorescences that are positioned above the foliar plane on strong scapes.
6. Ovate-cordate spathes that are reddish orange in color with white-colored venation.
7. Yellow to yellowish white to white-colored spadices.

Plants of the new *Anthurium* differ primarily from plants of the female parent selection in the following characteristics:

1. Spathe apices of plants of the new *Anthurium* are rounded with a mucronate tip whereas spathe apices of plants of the female parent selection are acuminate.
2. Developing spadix apices of plants of the new *Anthurium* are yellowish green in color whereas developing spadix apices of plants of the female parent selection are light pink in color.

Plants of the new *Anthurium* differ primarily from plants of the male parent selection in the following characteristics:

1. Plants of the new *Anthurium* have larger leaves than plants of the male parent selection.
2. Spathes of plants of the new *Anthurium* are slightly concave to concave whereas spathes of plants of the male parent selection are convex.
3. Spadices of plants of the new *Anthurium* are straight whereas spadices of plants of the male parent selection are incurved.

Plants of the new *Anthurium* can also be compared to plants of *Anthurium andreanum* 'ANTHIHPIXG', disclosed in U.S. Plant Pat. No. 34,200. In side-by-side comparisons, plants of the new *Anthurium* differ primarily from plants of 'ANTHIHPIXG' in the following characteristics:

1. Plants of the new *Anthurium* have larger leaves than plants of 'ANTHIHPIXG'.
2. Plants of the new *Anthurium* have larger spathes than plants of 'ANTHIHPIXG'.
3. Plants of the new *Anthurium* have longer spadices than plants of 'ANTHIHPIXG'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2636445' grown in a container.

Figure 2:
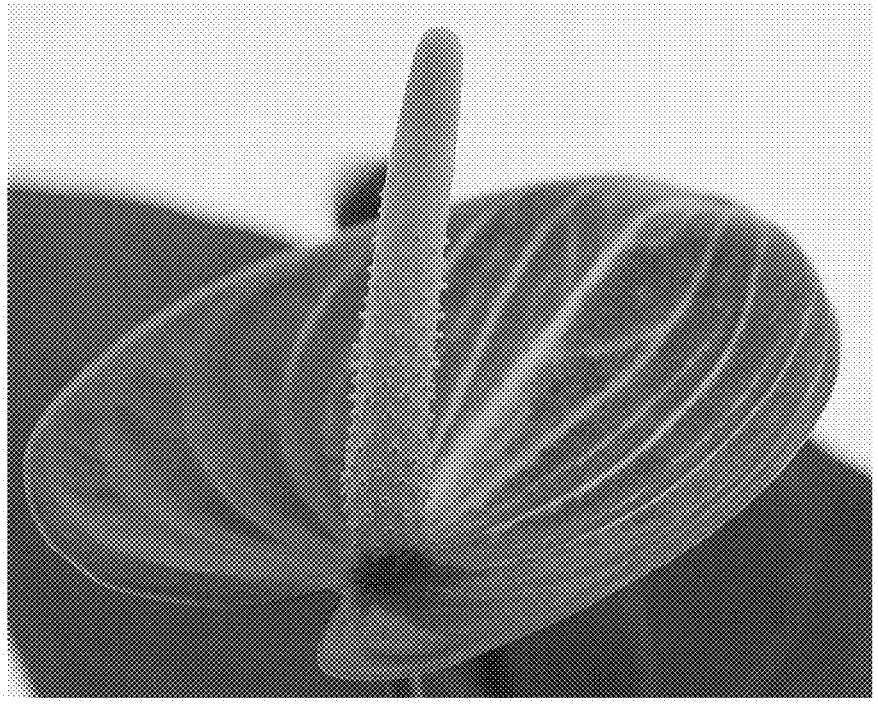

The photograph on the second sheet (FIG. 2) is a close-up view of a typical inflorescence of 'AN2636445'.

DETAILED BOTANICAL DESCRIPTION

The aforementioned photographs and following observations and measurements describe plants grown in 14-cm containers during the winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were eleven months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2636445'.

Parentage:

*Female, or seed, parent*.—Proprietary breeding selection of *Anthurium andreanum* identified as code number 11-026533-0004, not patented.

*Male, or pollen, parent*.—Proprietary breeding selection of *Anthurium andreanum* identified as code number 11-026521-0004, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading plant habit; overall shape, roughly spherical.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 24.9 cm.

*Plant height, from soil level to top of inflorescences*.—About 30.5 cm.

*Plant diameter or spread*.—About 39.4 cm.

Leaf description:

*Arrangement*.—Alternate; simple.

*Length*.—About 13.9 cm.

*Width*.—About 9 cm.

*Shape*.—Ovate-cordate.

*Apex*.—Apiculate to caudate with a mucronate tip.

*Base*.—Moderately to deeply cordate; occasionally, close to auriculate.

*Margin*.—Entire.

*Texture, upper and lower surfaces*.—Smooth, glabrous; moderately coriaceous.

*Venation pattern*.—Pinnate.

*Color*.—Developing leaves, upper surface: Close to 146B. Developing leaves, lower surface: Close to 146D; midvein, close to 145A. Fully expanded leaves, upper surface: Close to 147A; mucronate tip, close to N144A; venation, close to 144B. Fully expanded leaves, lower surface: Close to 146B; venation, close to N144A.

*Petioles*.—Length: About 16.1 cm. Diameter: Distally, about 3 mm and proximally, about 4 mm. Texture, upper and lower surfaces: Smooth, glabrous. Color, upper surface: Close to 144B. Color, lower surface: Close to 144C. Geniculum length: About 1.9 cm. Geniculum diameter: About 4 mm. Geniculum texture, upper and lower surfaces: Smooth, glabrous. Geniculum color, upper surface: Close to 144B. Geniculum color, lower surface: Close to 144C. Wing length: About 1.8 cm. Wing diameter: About 4 mm. Wing texture: Smooth, glabrous. Wing color: Close to 145C.

Inflorescence description:

*Inflorescence arrangement and flowering habit.*—Spathes with spadices; open inflorescences held above the foliar plane on strong scapes; flowering structures arise from leaf axils; freely and continuous flowering year-round in controlled temperature greenhouses in The Netherlands; typically about five developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 7.5 cm. Width: About 7.8 cm. Shape: Ovate-cordate; slightly concave to concave. Apex: Rounded with a mucronate tip. Base: Rounded cordate. Margin: Entire. Aspect: About 65° to 75° from the scape axis. Texture, upper and lower surfaces: Smooth, glabrous; moderately coriaceous. Color: When developing, front surface: Close to 44B; mucronate tip, close to NN155A; venation and areas adjacent to veins, close to NN155D. When developing, rear surface: Close to 41A; towards the base, close to 39B; mucronate tip, close to 150D; venation and areas adjacent to veins, close to NN155D. Fully developed, front surface: Close to 40A; mucronate tip, close to 155A; venation and areas adjacent to veins, close to NN155B; with subsequent development, main color becoming closer to 40B. Fully developed, rear surface: Close to 48C; towards the apex, close to 44C; mucronate tip, close to 155A; venation and areas adjacent to veins, close to 155C; with subsequent development, main color becoming closer to 41C.

*Spadices*.—Length: About 4.8 cm. Diameter: About 8 mm. Shape: Cylindrical, slightly tapering towards the apex; apex, obtuse; base, obtuse; in cross-section, rounded. Aspect: About 20° from the scape axis. Color: Immature: Close to 6C; apex, close to 144A; at the base, close to 12A. Mature: Close to a blend of 155A and 158C. Flowers: Type: Hermaphroditic. Quantity per spadix: About 200.Height: Less than 1 mm. Diameter: About 2 mm. Shape: Roughly square. Anther color: Close to 155D. Pollen amount: Scarce. Pollen color: Close to a blend of 155A and 158C. Stigma color: Close to 158D.

*Scapes*.—Length: About 24.3 cm. Diameter: About 3 mm. Strength: Strong, sturdy. Aspect: About 10° from vertical. Color: Close to 144A; distally, occasionally tinged with close to N170A; at the connection to the spathe, tinged with close to 41A to 41C.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2636445' as herein illustrated and described.

* * * * *